(12) United States Patent
Cho et al.

(10) Patent No.: US 7,875,748 B2
(45) Date of Patent: Jan. 25, 2011

(54) COMPOUND DERIVED FROM CYCLOPENTADIENONE, PREPARATION METHOD THEREOF AND EL ELEMENT USING THE SAME

(75) Inventors: Hyun-Nam Cho, Seoul (KR); Sung Hyun Jung, Seoul (KR); Seok-Jin Park, Seoul (KR); Seung-Eun Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 12/418,708

(22) Filed: Apr. 6, 2009

(65) Prior Publication Data

US 2009/0240062 A1 Sep. 24, 2009

Related U.S. Application Data

(62) Division of application No. 10/937,906, filed on Sep. 10, 2004, now abandoned.

(30) Foreign Application Priority Data

Sep. 27, 2003 (KR) ...................... 10-2003-0067197

(51) Int. Cl.
    C07C 243/20 (2006.01)
(52) U.S. Cl. .................................................... 564/251
(58) Field of Classification Search ...................... None
    See application file for complete search history.

(56) References Cited

FOREIGN PATENT DOCUMENTS

| JP | 1994-228553 | * | 8/1994 |
|----|-------------|---|--------|
| JP | 2002316955  |   | 10/2002 |

OTHER PUBLICATIONS

Mark T. Bernius, et al., "Progress with Light-Emitting Polymers" Adv. Mater. 2000, 12 No. 23, pp. 1737-1750.
Arno Kraft et al., "Electroluminescent Conjugated Polymers-Seeing Polymers in a new Light", Angew. Chem. Int. Ed. 1998, 37, 402-428.
Chihaya Adachi, et al.., "Blue light-emitting organic electroluminescent devices", Appl. Phys. Lett. 56(9), Feb. 1990, 799-801.
Junji Kido et al., "A Novel Electroluminescent Metal Complex: Tris(4-phenanthridinolato)aluminum(III)", Chemistry Letters 1997, pp. 593-594.
Michael A. Ogliaruso et al., "Chemistry of Cyclopentadienones", Chemical Reviews, vol. 65, No. 3, 1965, pp. 261-367.
Yuji Hamada, "The Development of Chelate Metal Complexes as an Organic Electroluminescent Material" IEEE Transactions on Electron Devices, vol. 44, No. 8, Aug. 1997, pp. 1208-1217.

Yasuhiko Shirota "Organic materials for electronic and optoelectronic devices", J. Mater. Chem., 2000, 10, 1-25.
Michael A. Ogliaruso, et al., "Bistetracyclones" and "Bishexaphenylbenzenes", Bisterracyclones, Oct. 1963, vol. 28, pp. 2725-2728.
Michael A. Ogliaruso et al., "Bistetracyclones and Bishexaphenylbenzenes. II" Bistetracyclones and Bishexaphynylbenzenes II, vol. 30, Oct. 1965, pp. 3354-3360.
H. Mukamal, et al., "Diels-Alder Polymers. III. Polymers Containing Phenylated Phenylene Units", Journal of Polymer Science, (1967), vol. 5, 2721-2729.
J. K. Stille et al., "Catenation and Kinetics of the Diels-Alder Step-Gowth Reaction in the Synthesis of Phenylated Polyphenylenes1", Synthesis of Phenylated Polyphenylenes, vol. 5, No. 1, Jan.-Feb. 1972, vol. 5 No. 1, pp. 49-55.
Uday Kumar et al., "Diels-Alder Polymerization between (bis(cyclopentadienones) and Acetylenes. A versatile Route to New Highly Aromatic Polymers", Macromolecules, 1995, 28, 124-130.
L.S. Hung et al., "Recent progress of molecular organic electroluminescent materials and devices", Materials Science and Engineering R 39 (2002) 143-222.
R.H. Friend, et al., "Electroluminescence in conjugated polymers", Nature, vol. 397, Jan. 1999, pp. 121-128.
M.A. Baldo, et al., "High-efficiency fluorescent organic light-emitting devices using aphosphorescent sensitizer", Nature, vol. 403, Feb. 2000, pp. 750-753.
J.K. Stille et al., "Diels-Alder polymerization: polymers containing controlled aromatic segments", Polymer Letters, vol. 4, (1966), pp. 791-793.
W. Wrasidlo, et al., "Preparation of poly(octaphenyl-tetraphenylene)", Polymer Letters, vol. 7, (1969), pp. 519-523.
D.Y. Kim, et al., "Blue light emitting polymers", Prog. Polym. Sci. 25 (2000), 1089-1139.
Teruichi Watanabe et al., "Optimization of emitting efficiency in organic LED cells using Ir comples" Synthetic Metals 122 (2001), 203-207.

* cited by examiner

*Primary Examiner*—Golam M. M. Shameem
*Assistant Examiner*—Alicia L Otton
(74) *Attorney, Agent, or Firm*—Fish & Richardson P.C.

(57) ABSTRACT

Disclosed are compounds represented by formula (1),

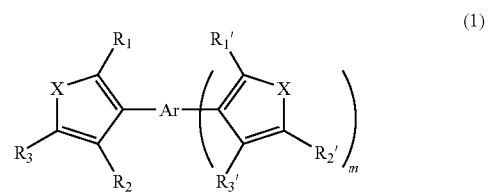

(1)

wherein m, X, $R_1$, $R_2$, $R_3$, $R_1'$, $R_2'$, $R_3'$, and Ar are described herein. The inventive cyclopentadienone compounds can be used as core materials for an organic electroluminescence element or other optical devices. The invention also describes methods for preparing compounds of formula (1).

5 Claims, 6 Drawing Sheets

COMPOUND DERIVED FROM CYCLOPENTADIENONE, PREPARATION METHOD THEREOF AND EL ELEMENT USING THE SAME

This application is a divisional of U.S. patent application Ser. No. 10/937,906 filed on Sep. 10, 2004 now abandoned and is hereby incorporated by reference in its entirety.

BACKGROUND OF THE INVENTION

1. Field of the Invention

The present invention relates to a compound derived from cyclopentadienone, which can be used as a core material for an organic electroluminescence (referred to as 'EL', hereinafter) element or for other optical devices, to a preparation method thereof, and to an EL element using the same.

2. Description of the Background Art

Since green light-emitting phenomenon using tris(8-hydroxy-quinolinato)aluminum (referred to as 'Alq3', hereinafter) as a light-emitting material has been known by Tang et al. (See *Appl. Phys. Lett.*, 51, p 913 (1987)) of Eastman Kodak, USA, numerous organic compounds for organic EL materials have been developed.

Currently used light-emitting materials are divided into a metal complex such as Alq3 well known as a fluorescent material (See *Chem. Lett.*, p. 593 (1997); and IEEE Trans Electron Devices, 44, p. 1208 (1997)), and a phosphorescent material (See *Nature*, 403, p. 750 (2000); and *Synth. Met.*, 122, p. 203 (2001)). Various organic compounds have been reported as an organic single molecule light-emitting material or a core material for other organic ELs (See *Chem. Rev.*, 171, p. 161 (1998); *Phys. World*, 12, p. 27 (1999); *J. Mater. Chem.*, 10, p. 1 (2000); and *Mater. Sci. Eng.*, R39, p. 143 (2002)).

Aside from the organic single molecule light-emitting material, many researches have been conducted on polymer-based light-emitting materials. For example, since professor Friend et al. in Cambridge university of United Kingdom reported first light-emitting phenomenon of poly(phenylenevinylene) (*Nature*, 347, p. 539 (1990)), a lot of polymer light-emitting materials have been reported (See *Angew. Chem. Int.* Ed., 37, p. 402 (1998); *Nature*, 397, p. 121 (1999); *Prog. Polym. Sci.*, 25, p. 1089 (2000); and *Adv. Mater.*, 12, p. 1737 (2000)).

Examples in which a cyclopentadienones or its derivative is used as an organic EL material are exceedingly rare, but there is an example that a cyclopentadienone compound substituted with a phenyl group is used as a light-emitting material (*Appl. Phys. Lett.*, 56, p. 799 (1990)). In addition, there is an example that a polyphenylene group polymer substituted with a plurality of phenyl groups (See *J. Polym. Sci.*, Part B. 4, p. 791 (1966); *J. Polym. Sci.*, Part A-1, 5, p. 2721 (1967); *J. Polym. Sci.*, Part B, 7, p. 519 (1969); *Macromolecules*, 5, p. 49 (1972); *Macromolecules*, 28, p. 124 (1995); *Macromolecules*, 33, p. 3535 (2000)), which is obtained by a polymerization of a compound having bis-acetylene group (or referred to as 'diethynyl group') and a compound having bis-cyclopentadienone group (See *J. Org. Chem.*, 28, p 2725 (1963); *Chem. Rev.*, 65, p 261 (1965); *J. Org. Chem.*, 30, p 3354 (1965); and U.S. Pat. No. 4,400,540) through Diels-Alder reaction, is used as a light-emitting material.

However, it has only been reported that such polymers can be applied as a photoreceptor (See U.S. Pat. No. 5,882,829) or as a dielectric (See U.S. Pat. No. 5,965,679) in a microelectronics industry, especially in the field of integrated circuits. That is, there are few known as compounds derived from cyclopentadienone, and there are even fewer examples that such compounds are used as an organic EL material.

SUMMARY OF THE INVENTION

Therefore, an object of the present invention is to provide a compound derived from cyclopentadienone, which can be used as an organic light-emitting material, a preparation method thereof, and an EL element using the same.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a unit of this specification, illustrate embodiments of the invention and together with the description serve to explain the principles of the invention.

In the drawings.

DETAILED DESCRIPTION OF THE PREFERRED EMBODIMENTS

Figure 1:
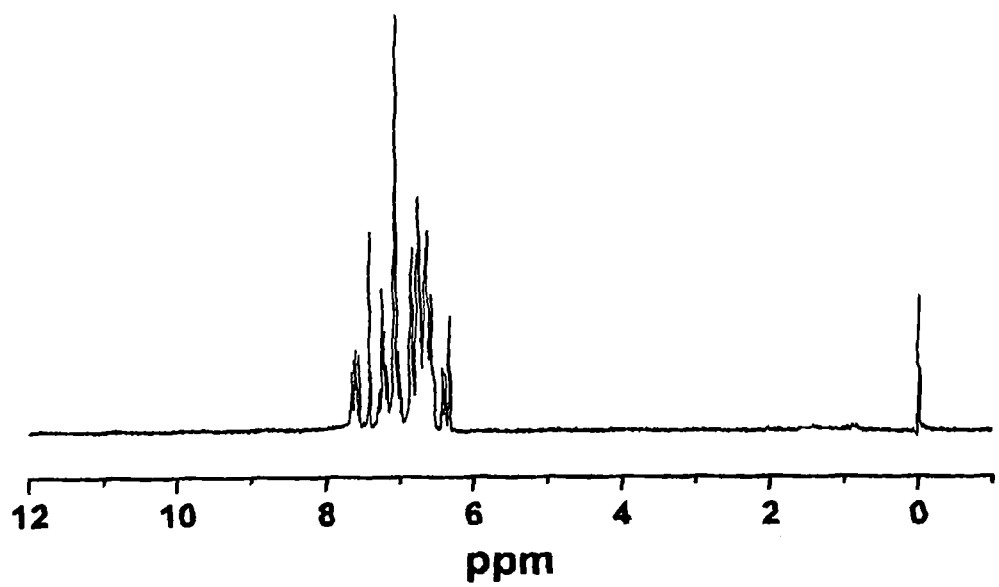
FIG. 1 is $^1$H NMR spectrum of the compound [M-5]

As a result of carrying out constant researches in order to use a compound derived from cyclopentadienone as an organic EL material, the inventors of the present invention have synthesized novel compounds through various reactions, and discovered that they can be used as a light-emitting material for an organic EL element.

Therefore, the present invention is directed to a compound derived from a compound having one or more cyclopentadienone group, which is represented by the following formula (1), to a preparation method thereof, and to an organic EL element using the same

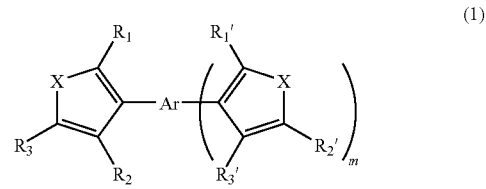

(1)

wherein m is an integer of 0-5;

X is S, $CR_1R_2$, $CR_1=C[[R_1]]R_2$, $C=NR_1$ or $C=NNR_1R_2$;

$R_1$, $R_2$, $R_3$, $R_1'$, $R_2'$ and $R_3'$ may be the same with or different from each other, and independently selected from the group consisting of hydrogen, $C_1$-$C_{22}$ aliphatic alkyl group, $C_1$-$C_{22}$ alicyclic alkyl and alkoxy group, and $C_6$-$C_{18}$ aryl and aryloxy; and Ar is an aromatic or heteroaromatic group selected from the group consisting of phenylene, naphthalene, anthracene, fluorene, thiophene, pyrrole, pyridine, aryloxadiazole, triazole, carbazole, arylamine, arylsilane and derivatives thereof, but not limited thereto.

More specifically, $R_1$, $R_2$, $R_3$, $R_1'$, $R_2'$ and $R_3'$ may be independently selected from the group consisting of hydrogen, methyl, ethyl, propyl, isopropyl, butyl, isobutyl, pentyl, hexyl, ethylhexyl, heptyl, octyl, isooctyl, nonyl, decyl, dodecyl, hexadecyl, octadecyl, docoxyl, cyclopropyl, cyclopentyl, cyclohexyl, methoxy, ethoxy, butoxy, hexyloxy, methoxy-ethoxyethyl, methoxy-ethoxyethoxyethyl, cyanoethyl, carboxymethyl, phenyl, phenoxy, tolyl, benzyl, naphthyl, anthrancenyl and derivatives thereof, and preferable examples of Ar include substituents having the following structures:

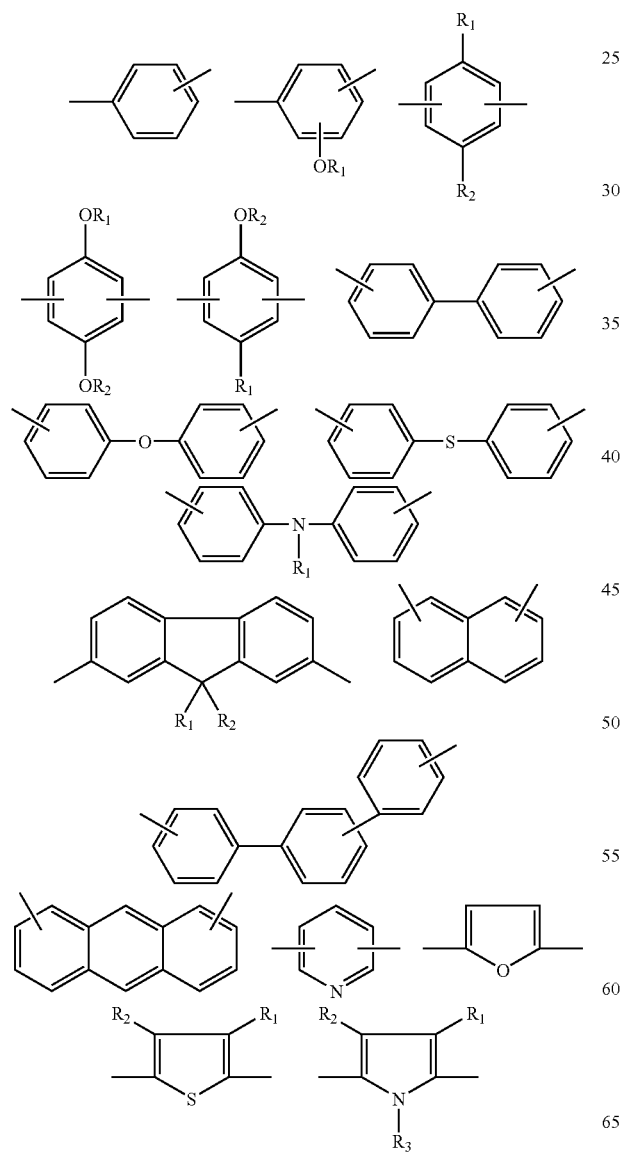

-continued

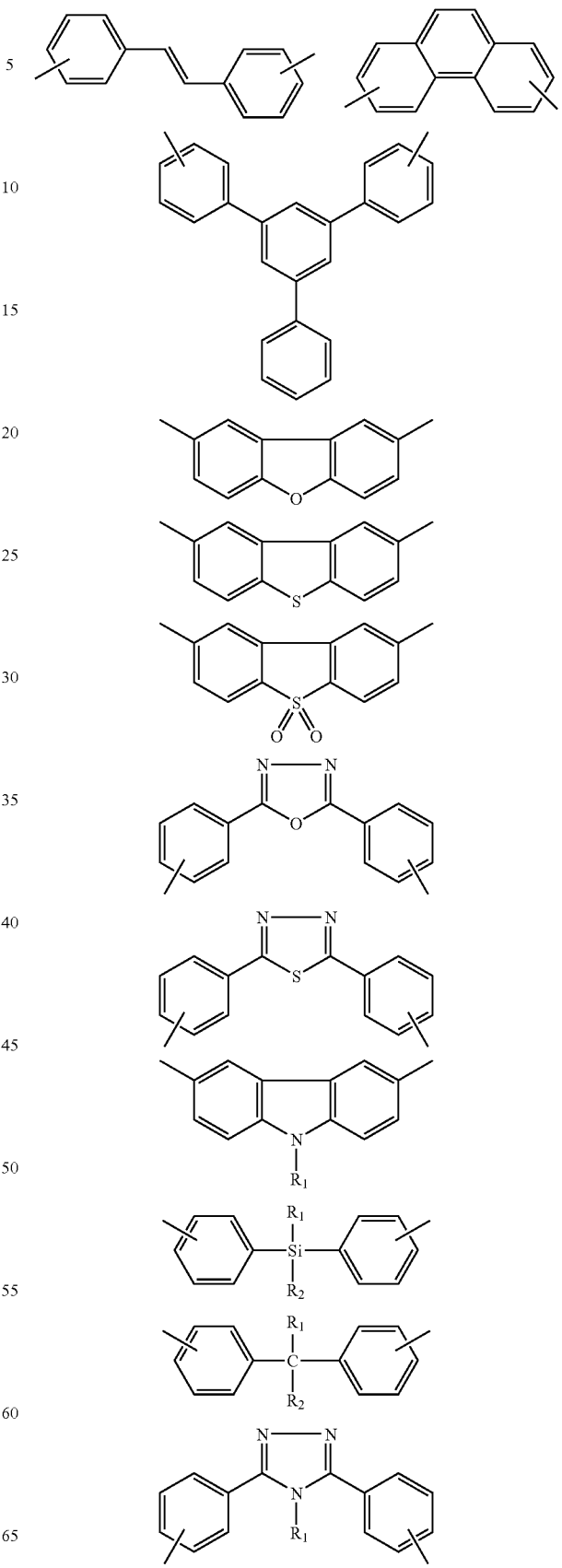

-continued

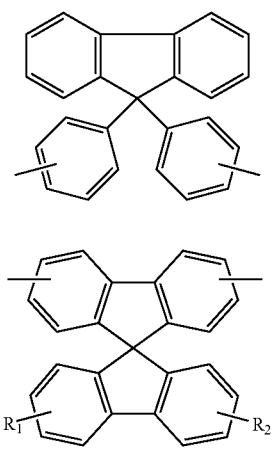

wherein $R_1$, $R_2$ and $R_3$ are the same as defined in the above formula (1).

The compound of the formula (1) in accordance with the present invention can be prepared by various reactions, for example, as shown in the following Reaction Schemes 1 to 4 using the compound represented by the following formula (3) or (4) as a starting material:

(3)

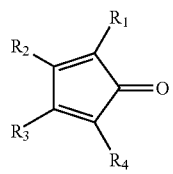

(4)

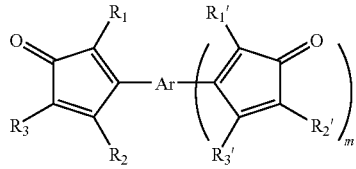

Reaction Scheme 1

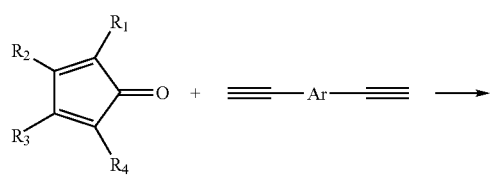

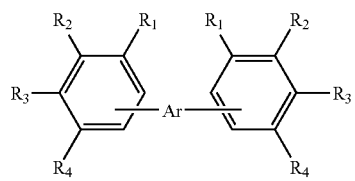

Reaction Scheme 2

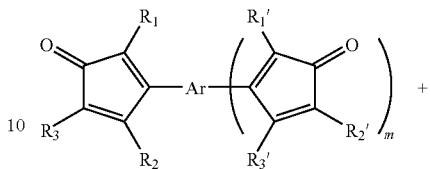

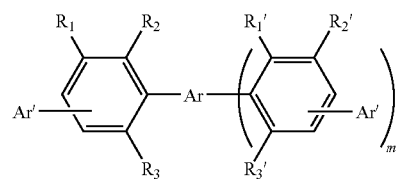

Reaction Scheme 3

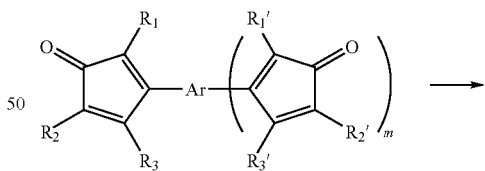

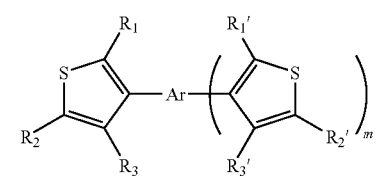

Reaction Scheme 4

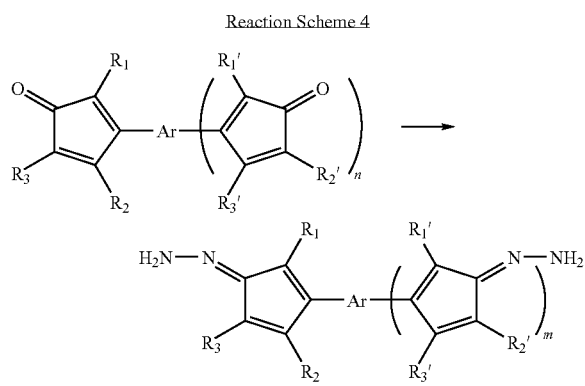

In formulae (3) and (4), and Reaction Schemes 1 to 4, m, $R_1$, $R_2$, $R_3$, $R_1'$, $R_2'$, $R_3'$ and Ar are the same as those defined in formula (1), and Ar' is the same as Ar as defined in formula (1), but Ar and Ar' may be different from each other. $R_4$ is the same as those defined for $R_1$, $R_2$ and $R_3$.

In preparation of the compound of formula (1) in accordance with the present invention, besides the methods through reactions represented by the above Reaction Schemes 1 to 4, it can be prepared using any starting materials through any routes, so long as the final products are the same. In other word, in preparation of the compound of formula (1), it is not necessary to specifically limit a starting material, a solvent, a reaction temperature, concentration, a catalyst or the like, and likewise yield of the product.

The present invention is also directed to an application of the compound of formula (1) as a material for an organic EL element or other optical devices. Thus, the organic EL element or other optical devices in accordance with the present invention comprise the compound represented by formula (1) as a core material.

In the present invention, the organic EL element and other optical devices using the compound represented by formula (1) can be prepared by any conventional methods known in the art. In a typical method, the compound of the present invention may be formed into a thin film by a well-known method such as vacuum depositing or spin coating, and such film may be directly used as an EL material.

In construction, an EL element according to the present invention can include not only a typical type of anode/light-emitting layer/cathode, in which a light-emitting layer material is inserted between an anode and a cathode, but also a type of anode/hole transport layer/light-emitting layer/electron transport layer/cathode, or a type of anode/electron injection layer/hole transport layer/light-emitting layer/electron transport layer/electron injection layer/cathode, in which a hole transport layer and/or an electron transport layer (See Japanese Laid-Open Patent Publication Nos. 2-135361; 3-152184; and 6-207170) are also used. However, in the present invention, there is no limitation on the construction of an EL element.

As an anode, a material in which a metal or metallic oxide such as indium-tin oxide (refer to as 'ITO', hereinafter), gold, copper, tin oxide or zinc oxide, or an organic semi-conducting compound such as polypyrrole, polyaniline or polythiophene is coated onto a transparent substrate such as glass, transparent plastic or quartz usually at a thickness of 10 nm to 1 μm can be used. As a cathode, a metal such as sodium, magnesium, calcium, aluminum, indium, silver, gold or copper, or alloys thereof can be used.

Examples of a hole transport layer may include polyvinylcarbazole, 2,5-bis(4'-diethylaminophenyl)-1,3,4,-oxadiazole or N,N'-diphenyl-N,N'-(3-methyl-phenyl)-1,1'-biphenyl-4,4'-diamine (TPD), and examples of an electron transport layer may include any known compound such as tris(8-hydroxyquinolinato)aluminum, 2-(4'-tert-butylphenyl)-5-(4''-biphenyl)-1,3,4-oxa-diazole or 2,4,7-trinitro-9-fluoreneone. Those compounds may be used in the form of a thin film by applying them with any known thin film forming method, for example, vacuum depositing, spin coating, casing or LB method.

EXAMPLES

The present invention will now be described in more detail with reference to the following examples. However, examples are to illustrate the present invention, not to limit the scope of the present invention thereto.

Example 1

Reaction of tetraphenylcyclopentadienone with 1,4-diethynyl-2,5-dimethoxybenzene (Synthesis of [M-1])

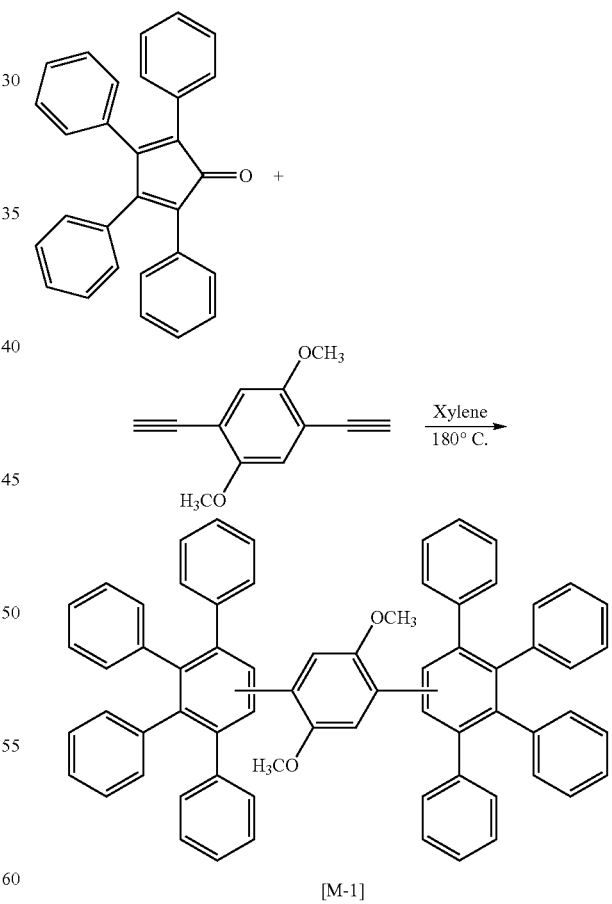

[M-1]

2.0 g (5.25 mmol) of tetraphenylcyclopentadienone and 0.27 g (2.5 mmol) of 1,4-diethynyl-2,5-dimethoxybenzene were put into a 100 ml two-neck round bottom flask equipped with a stirrer, a thermometer and a reflux condenser under an argon atmosphere, and 50 ml of xylene was added thereto.

The temperature of the reaction mixture was gradually raised to 180° C., and then, the resultant was stirred at 180° C. for 24 hours. When the reaction was completed, the reaction mixture was cooled down to room temperature and then gradually dropped into ethanol, to obtain white solid. The solid was filtered, dried and re-crystallized from a mixture of chloroform/ethanol to obtain white solid. This solid was filtered and then dried sufficiently in a vacuum oven at 40° C. to give 0.84 g (37% yield) of [M-1], of which melting point was 340-342° C.

$^1$H NMR (CDCl$_3$), δ=3.28(s, 6H, —OCH$_3$) 6.58-7.58 (m, 44H, aromatic)

Ultraviolet (hereinafter, referred to as 'UV') absorption maximum wavelength of the product in chloroform was 305 nm, and maximum PL wavelength was 410 nm.

Example 2

Reaction of 7,9-diphenyl-8H-cyclophene[a]acenaphtylene-8-one with 1,4-diethynyl-2,5-dimethoxybenzene (Synthesis of [M-2])

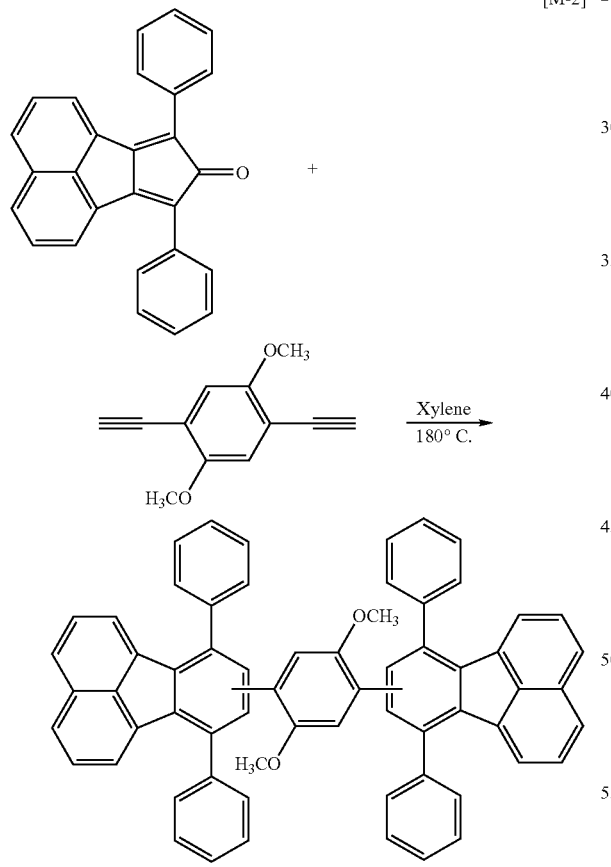

1.42 g (4 mmol) of 7,9-diphenyl-8H-cyclophene[a]acenaphtylene-8-one and 0.22 g (2 mmol) of 1,4-diethynyl-2,5-dimethoxybenzene were put into a 100 ml two-neck round bottom flask equipped with a stirrer, a thermometer and a reflux condenser under an argon atmosphere, and 50 ml of xylene was added thereto. The temperature of the resultant was gradually raised to 180° C., and then the reaction mixture was stirred at 180° C. for 24 hours. When the reaction was completed, the reaction mixture was cooled down to room temperature and then gradually dropped into ethanol to obtain a light green solid. This solid was filtered, dried and then re-crystallized from a mixture of chloroform/ethanol to obtain a light green solid. This solid was filtered, and then dried sufficiently in a vacuum oven at 40° C. to give 0.69 g (40% yield) of [M-2], of which melting point was 370-372° C.

$^1$H NMR (CDCl$_3$), δ=3.44(s, 6H, —OCH$_3$) 6.58-8.14 (m, 36H, aromatic).

In chloroform, maximum UV absorption wavelength of the product was 335 nm, and maximum PL wavelength was 470 nm.

Example 3

Reaction of 1,3-diphenyl-2H-cyclopenta[l]phenanthrene-2-one with 1,4-diethynyl-2,5-dimethoxybenzene (Synthesis of [M-3])

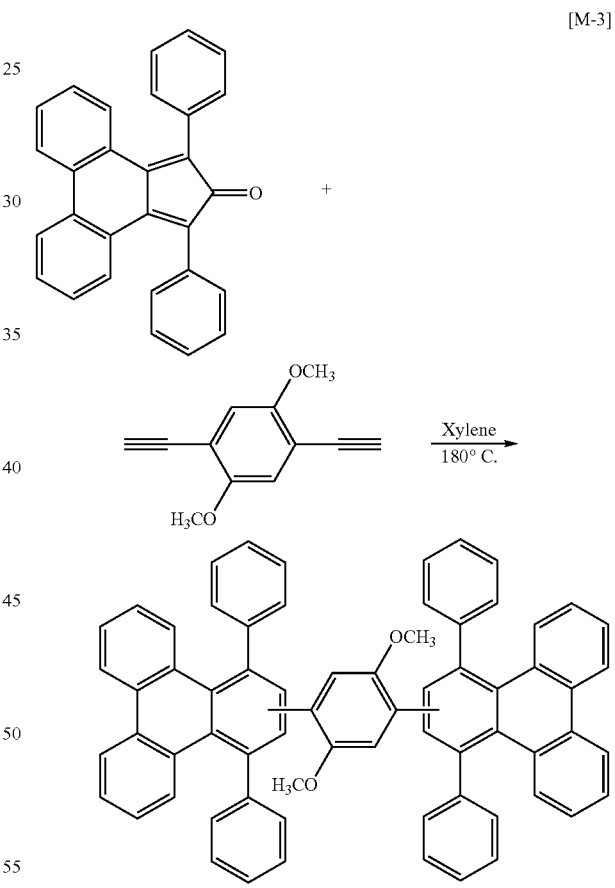

1.6 g (4 mmol) of 1,3-diphenyl-2H-cyclopenta[l]phenanthrene-2-one and 0.22 g (2 mmol) of 1,4-diethynyl-2,5-dimethoxybenzene were put into a 100 ml two-neck round bottom flask equipped with a stirrer, a thermometer and a reflux condenser under an argon atmosphere, and 50 ml of xylene was added thereto. The temperature of the resultant was gradually raised to 180° C., and the resultant was stirred at 180° C. for 24 hours. When the reaction was completed, the reaction mixture was cooled down to room temperature and then gradually dropped into ethanol to obtain white solid.

This solid was filtered, dried and then re-crystallized from a mixture of chloroform/ethanol to obtain white solid. This solid was filtered, and then dried sufficiently in a vacuum oven at 40° C. to give 0.59 g (35% yield) of [M-3], of which melting point was 379-381° C.

$^1$H NMR (CDCl$_3$), δ=3.12(s, 6H, —OCH$_3$), 6.46 (s, 2H, aromatic), 6.99-7.69 (m, 34H, aromatic), 8.37-8.42 (d, 4H, aromatic)

In chloroform, maximum UV absorption wavelength of the product was 303 nm, and maximum PL wavelength was 420 nm.

Example 4

Reaction of tetraphenylcyclopentadienone with 2,7-diethynyl-9,9'-di-n-hexylfluorene (Synthesis of [M-4])

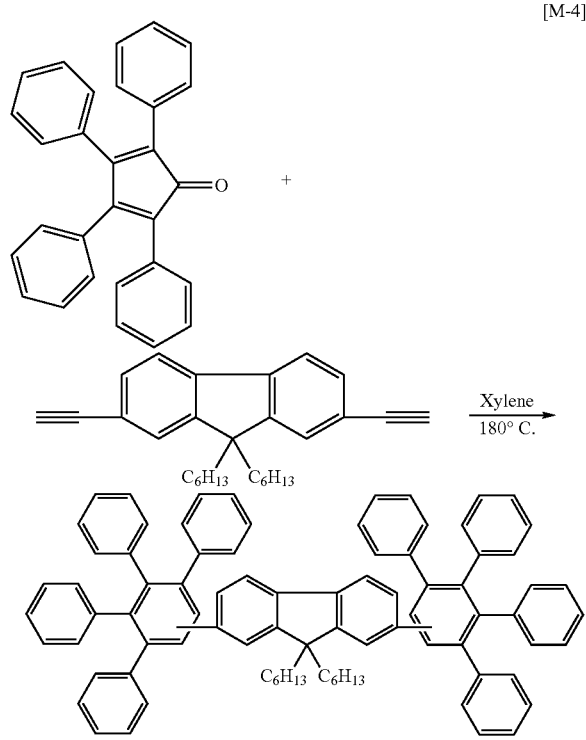

0.5 g (1.3 mmol) of tetraphenylcyclopentadienone and 1.27 g (3.3 mmol) of 2,7-diethynyl-9,9'-di-n-hexylfluorene were put into a 100 ml two-neck round bottom flask equipped with a stirrer, a thermometer and a reflux condenser under an argon atmosphere, and 10 ml of xylene was added thereto. The temperature of the resultant was gradually raised to 180° C., and the reaction mixture was then stirred at 180° C. for 24 hours. When the reaction was completed, the reaction mixture was cooled down to room temperature and then gradually dropped into a mixture of acetone/methanol (800 ml/200 ml), so as to precipitate a solid. The precipitated solid was filtered, dissolved in chloroform again and re-precipitated into methanol, to obtain purified solid. This solid was filtered, thoroughly washed with methanol, and then dried sufficiently in a vacuum oven at 40° C. to give 1.06 g (75% yield) of white solid [M-4], of which melting point was 157-160° C.

$^1$H NMR (CDCl$_3$), δ=0.11-0.38 (br, s, CH$_3$), 0.76-1.22 (br, m, CH$_2$), 1.38-1.60(br, s, CCH$_2$), 6.65-7.61 (m, aromatic)

In chloroform, maximum UV absorption wavelength of the product was 327 nm, and maximum PL wavelength was 377 nm.

Example 5

Reaction of tetraphenylcyclopentadienone with 2,7-diethynyl-9,9'-spyrobifluorene (Synthesis of [M-5])

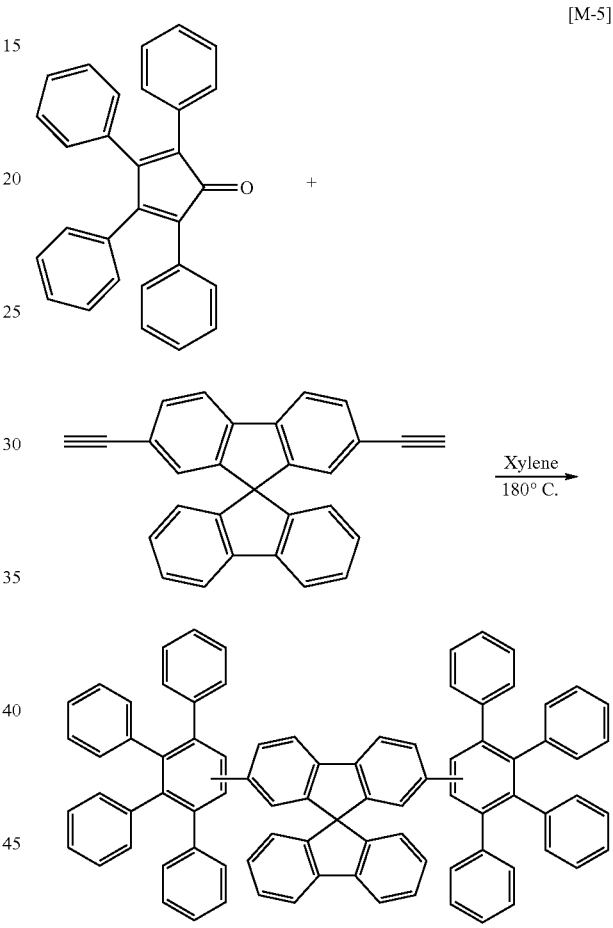

1.54 g (4 mmol) of tetraphenylcyclopentadienone and 0.72 g (2 mmol) of 2,7-diethynyl-9,9'-spyrobifluorene were put into a 100 ml two-neck round bottom flask equipped with a stirrer, a thermometer and a reflux condenser under an argon atmosphere, and 50 ml of xylene was added thereto. The temperature of the resultant was gradually raised to 180° C., and the reaction mixture was then stirred at 180° C. for 24 hours. When the reaction was completed, the reaction mixture was cooled down to room temperature and then gradually dropped into ethanol to obtain white solid. This solid was filtered, dried and then re-crystallized from a mixture of chloroform/ethanol to obtain white solid. This solid was filtered and then dried sufficiently in a vacuum oven at 40° C. to give 1.01 g (47% yield) of [M-5], of which melting point was 390-393° C. FIG. 1 shows $^1$H NMR spectrum of the compound [M-5].

¹H NMR (CDCl₃), δ=6.32-7.65 (m, 54H, aromatic)

In chloroform, maximum UV absorption wavelength of the product was 300 nm, and maximum PL wavelength was 416 nm.

Example 6

Reaction of 7,9-diphenyl-8H-cyclophene[a]acenaph-tylene-8-one with 2,7-diethynyl-9,9'-spyrobifluorene (Synthesis of [M-6])

¹H NMR (CDCl₃), δ=6.51-7.72 (m, 48H, aromatic)

In chloroform, maximum UV absorption wavelength of the product was 310 nm, and maximum PL wavelength was 420 nm.

Example 7

Reaction of 1,3-diphenyl-2H-cyclopenta[l]phenan-threne-2-one with 2,7-diethynyl-9,9'-spyrobifluorene (Synthesis of [M-7])

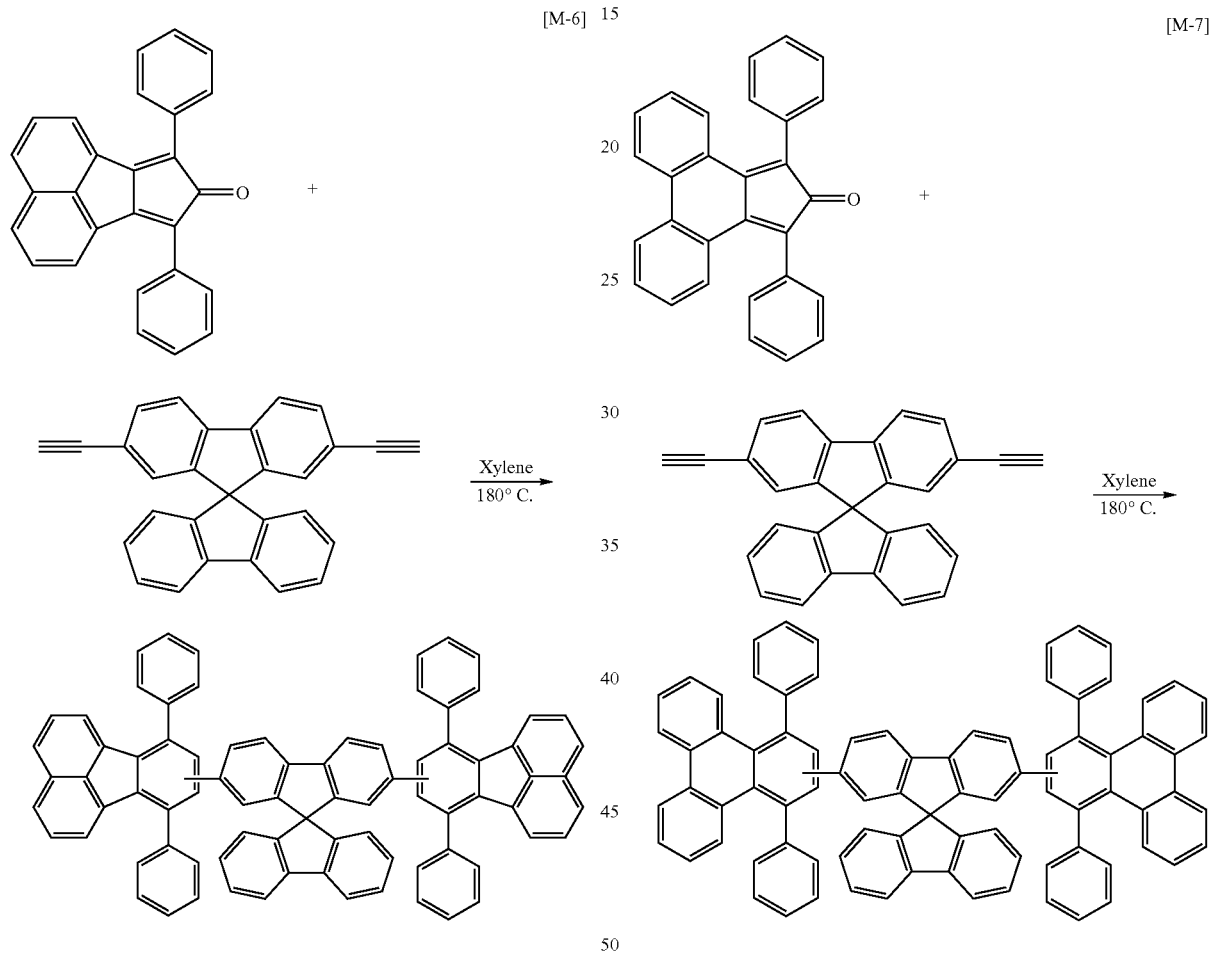

1.4 g (4 mmol) of 7,9-diphenyl-8H-cyclophene[a]acenaphtylene-8-one and 0.72 g (2 mmol) of 2,7-diethynyl-9,9'-spyrobifluorene were put into a 100 ml two-neck round bottom flask equipped with a stirrer, a thermometer and a reflux condenser under an argon atmosphere, and 50 ml of xylene was added thereto. The temperature of the resultant was gradually raised to 180° C., and the reaction mixture was then stirred at 180° C. for 24 hours. When the reaction was completed, the reaction mixture was cooled down to room temperature and then gradually dropped into ethanol to obtain yellow solid. This solid was filtered, dried and then re-crystallized from a mixture of chloroform/ethanol to obtain yellow solid. This solid was filtered and then dried sufficiently in a vacuum oven at 40° C. to give 0.96 g (47% yield) of [M-6], of which melting point was 330-331° C.

2.93 g (7.6 mmol) of 1,3-diphenyl-2H-cyclopenta[l]phenanthrene-2-one and 0.9 g (2.5 mmol) of 2,7-diethynyl-9,9'-spyrobifluorene were put into a 100 ml two-neck round bottom flask equipped with a stirrer, a thermometer and a reflux condenser under an argon atmosphere, and 50 ml of xylene was added thereto. The temperature of the resultant was gradually raised to 180° C., and the reaction mixture was then stirred at 180° C. for 24 hours. When the reaction was completed, the reaction mixture was cooled down to room temperature and then gradually dropped into ethanol to obtain white solid. This solid was filtered, dried and then re-crystallized from a mixture of chloroform/ethanol to obtain white solid. This solid was filtered and then dried sufficiently in a vacuum oven at 40° C. to give 1.15 g (43% yield) of [M-7], of which melting point was 392-394° C.

$^1$H NMR (CDCl$_3$), δ=7.46-8.13 (m, 52H, aromatic)

In chloroform, maximum UV absorption wavelength of the product was 312 nm, and maximum PL wavelength was 424 nm.

Example 8

Reaction of tetraphenylcyclopentadienone with 3,6-diethynyl-9-ethylcarbazol (Synthesis of [M-8])

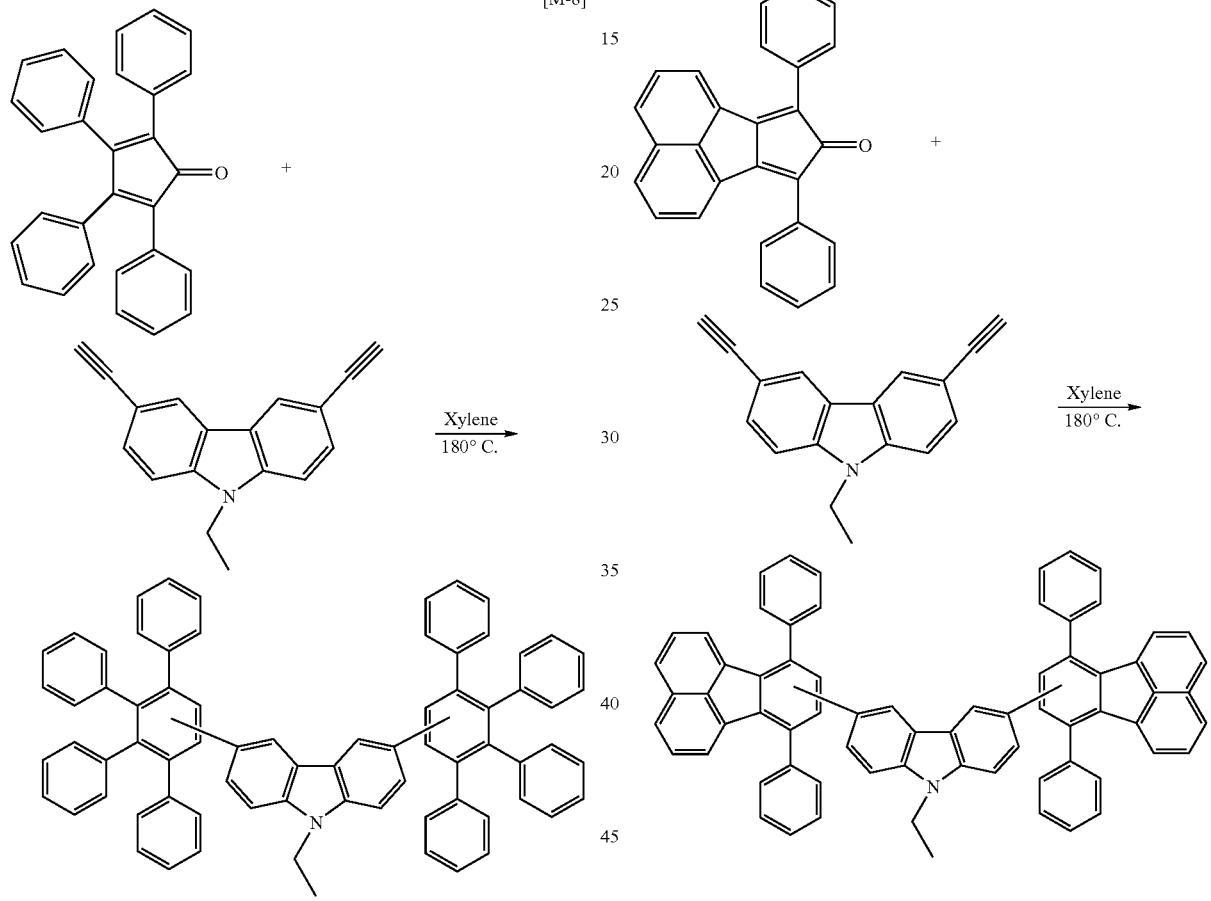

1.54 g (4 mmol) of tetraphenylcyclopentadienone and 0.39(2 mmol) of 3,6-diethynyl-9-ethylcarbazole were put into a 100 ml two-neck round bottom flask equipped with a stirrer, a thermometer and a reflux condenser under an argon atmosphere, and 50 ml of xylene was added thereto. The temperature of the resultant was gradually raised to 180° C., and the reaction mixture was then stirred at 180° C. for 24 hours. When the reaction was completed, the reaction mixture was cooled down to room temperature and then gradually dropped into ethanol to obtain brown solid. This solid was filtered, dried and then re-crystallized from a mixture of chloroform/ethanol to obtain brown solid. This solid was filtered and then dried sufficiently in a vacuum oven at 40° C. to give 0.66 g (33% yield) of [M-8], of which melting point was 280-283° C.

$^1$H NMR (CDCl$_3$), δ=1.43(t, 2H, —CH$_2$), 4.23 (q, 3H, CH$_3$), 6.91-7.30 (m, 44H, aromatic), 7.73 (s, 2H, aromatic), 7.95 (s, 2H, aromatic)

In chloroform, maximum UV absorption wavelength of the product was 313 nm, and maximum PL wavelength was 397 nm.

Example 9

Reaction of 7,9-diphenyl-8H-cyclophene[a]acenaph-tylene-8-one with 3,6-diethynyl-9-ethylcarbazole (Synthesis of [M-9])

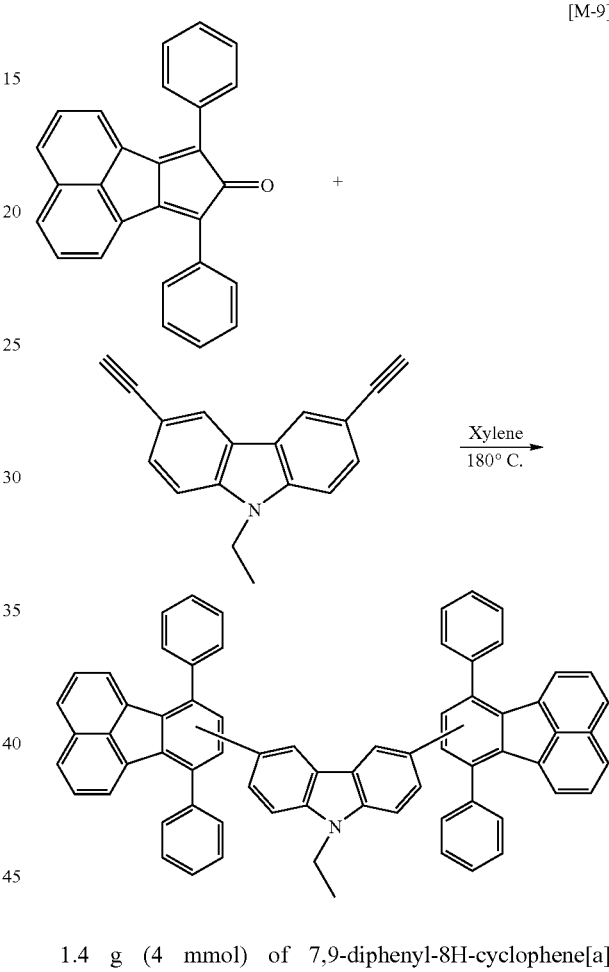

1.4 g (4 mmol) of 7,9-diphenyl-8H-cyclophene[a] acenaphtylene-8-one and 0.39 g (2 mmol) of 2,7-diethynyl-9-ethylcarbazole were put into a 100 ml two-neck round bottom flask equipped with a stirrer, a thermometer and a reflux condenser under an argon atmosphere, and 50 ml of xylene was added thereto. The temperature of the resultant was gradually raised to 180° C., and the reaction mixture was then stirred at 180° C. for 24 hours. When the reaction was completed, the reaction mixture was cooled down to room temperature and then gradually dropped into ethanol to obtain yellow solid. This solid was filtered, dried and then re-crystallized from a mixture of chloroform/ethanol to obtain yellow solid. This solid was filtered and then dried sufficiently in a vacuum oven at 40° C. to give [M-8] 0.68 g (35% yield) of [M-9], of which melting point was 275-276° C.

$^1$H NMR (CDCl$_3$), δ=1.43(t, 2H, —CH$_2$), 4.23 (q, 3H, CH$_3$), 6.74 (d, 2H, aromatic), 7.13-7.98 (m, 38H, aromatic)

In chloroform, maximum UV absorption wavelength of the product was 322 nm, and maximum PL wavelength was 480 nm.

Example 10

Synthesis of 2,7-bis(2,4,5-triphenylcyclopentadienon-3-yl)-9,9'-spyrobifluorene [M-12]

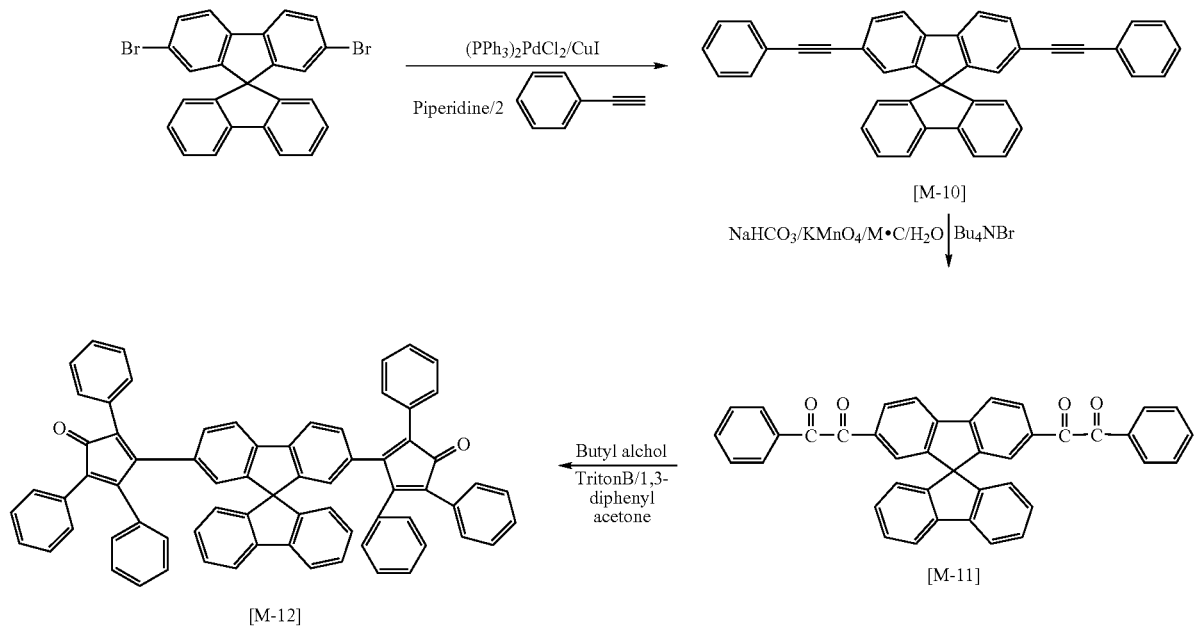

Synthesis of 2,7-bis(phenylethynyl)-9,9'-spyrobifluorene [M-10]

10 g (21.09 mmol) of 2,7-dibromo-9,9'-spyrobifluorene, 0.43 g (0.63 mmol) of bistriphenylphosphine palladium dichloride and 0.12 g (0.63 mmol) of copper iodide were put into a 500 ml three-neck round bottom flask equipped with a stirrer, a thermometer and a reflux condenser under an argon atmosphere, and then 300 ml of piperidine was added thereto so as to dissolve the resultant. 5.38 g (52.61 mmol) of phenylacetylene was gradually dropped thereto at room temperature. After completion of the dropping, the temperature of the reaction mixture was gradually raised to 110° C. and then stirred at 110° C. for 12 hours. When the reaction was completed, the reaction mixture was cooled down to room temperature. Generated salt was filtered off, and then the filtrate was concentrated under a reduced pressure. The residue was dissolved in dichloromethane, washed with water several times and then dried with anhydrous magnesium sulfate, which was then filtered off. The solvent was removed, and the residue was re-crystallized from a mixture of ethyl acetate and hexane to obtain yellow crystal, which was dried sufficiently in a vacuum oven at 40° C. to give 6.52 g (59.7% yield) of [M-10], of which melting point was 210-212° C.

$^1$H NMR (CDCl$_3$), δ=6.74-6.78 (d, 2H, aromatic), 6.90 (s, 2H, aromatic), 7.10-7.18 (t, 2H, aromatic), 7.24-7.28 (m, 6H, aromatic), 7.36-7.42 (m, 6H, aromatic), 7.52-7.57 (d, 2H, aromatic) 7.79-7.88 (t, 4H, aromatic).

Synthesis of 2,7-bis(phenylglyoxalyl)-9,9'-spyrobifluorene [M-11]

6.41 g (12.40 mmol) of [M-10] was put into a 1 L three-neck round bottom flask equipped with a stirrer and dissolved in 150 ml of dichloromethane, and 300 ml of water was then added thereto. 0.62 g of tetrabutylammonium bromide, 2.50 g of sodium bicarbonate and 12.50 g of potassium permanganate were added into the above reaction flask, and the resultant was stirred for 48 hours. When the reaction was completed, an ice-bath was installed, and then 18 g of sodium bisulfite and 9 ml of hydrochloric acid were gradually added to the reaction mixture, and the resultant was additionally stirred for 30 minutes. The reaction mixture was filtered, and filtrate was then extracted with dichloromethane. The organic extract was washed with water several times and then dried with anhydrous magnesium sulfate, and then solvent was removed to obtain yellow solid. This solid was re-crystallized from ethyl acetate to give yellow crystal, which was filtered and then dried sufficiently in a vacuum oven at 40° C. to give 3.61 g (50% yield) of [M-11], of which melting point was 134-136° C.

$^1$H NMR (CDCl$_3$), δ=6.67-6.70 (d, 2H, aromatic), 7.09-7.16 (t, 2H, aromatic), 7.38-7.63 (m, 10H, aromatic), 7.87-8.01 (m, 10H, aromatic).

Synthesis of 2,7-bis(2,4,5-triphenylcyclopentadienon-3-yl)-9,9'-spyro-bifluorene [M-12]

3.50 g (6.0 mmol) of [M-11] was put into a 1 L three-neck round bottom flask equipped with a stirrer, a thermometer and a reflux condenser under an argon atmosphere, and 350 ml of ethanol and 150 ml of butanol were added thereto, and the resultant was then heated to 120° C. so as to dissolve the starting material. To the resulting solution, 2.78 g (13.2 mmol) of 1,3-diphenyl-2-propaneone, 0.25 g of potassium hydroxide and 4.7 ml of water were added. The resultant was then reacted at 120° C. for 12 hours. After the reaction was completed, the temperature of the reaction mixture was gradually cooled down to 0° C. to give a dark brown solid, which was filtered and then washed with cold ethanol. After filtering, this solid was dried sufficiently in a vacuum oven at 40° C. to give 2.51 g (44.6% yield) of [M-12], of which melting point was 192-195° C.

$^1$H NMR (CDCl$_3$), δ=6.14(s, 1H, aromatic), 6.48-6.52 (d, 2H, aromatic), 6.73-6.76 (d, 3H, aromatic), 6.98-7.30 (m, 30H, aromatic), 7.47-7.60 (d, 4H, aromatic)

Example 11

Reaction of 2,7-bis(2,4,5-triphenylcyclopentadienon-3-yl)-9,9'-spyrobifluorene with 4-ethynyl-N,N-ditolylaniline (Synthesis of [M-13])

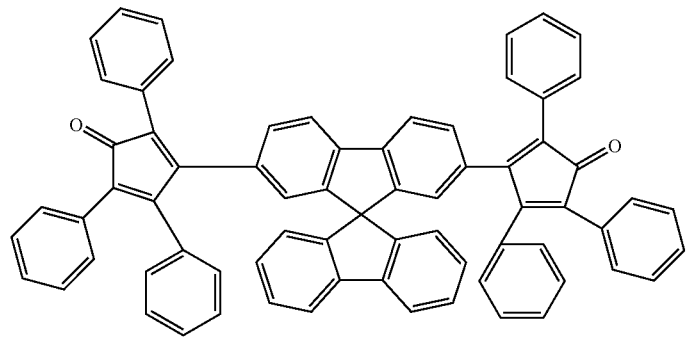

[M-12]

+

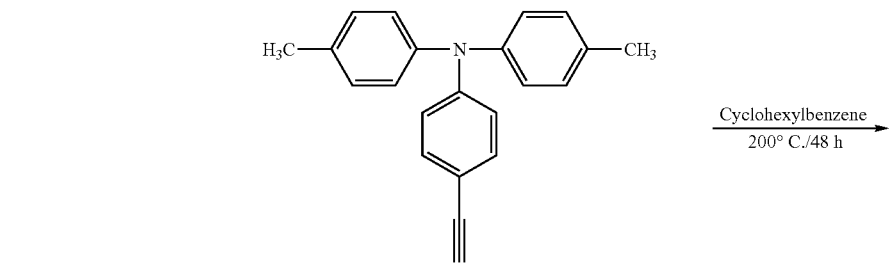

Cyclohexylbenzene
200° C./48 h

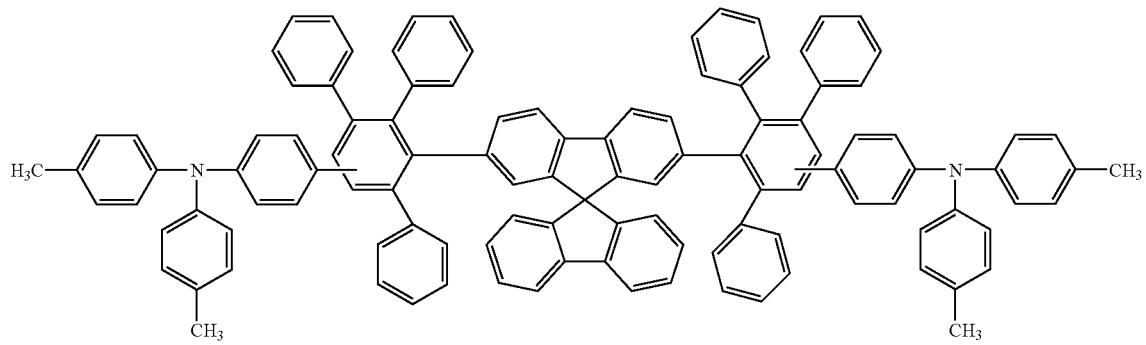

[M-13]

0.5 g (0.54 mmol) of 2,7-bis(2,4,5-triphenylcyclopentadienon-3-yl)-9,9'-sprobifluorene) and 0.48 g (1.61 mmol) of 4-ethynyl-N,N-ditolylaniline were put into a 100 ml two-neck round bottom flask equipped with a stirrer, a thermometer and a reflux condenser under an argon atmosphere, and 10 ml of cyclohexylbenzene was added thereto. The temperature of the reaction mixture was gradually raised to 200° C., and the resultant was then stirred at 200° C. for 24 hours. When the reaction was completed, the reaction mixture was cooled down to room temperature and then gradually dropped into a mixture of acetone/methanol (800 ml/200 ml), so as to precipitate a solid. The precipitated solid was filtered, dissolved in chloroform again, and then re-precipitated into methanol to give a purified solid. This solid was filtered, thoroughly washed with a methanol and then dried sufficiently in a vacuum oven at 40° C. to give 0.43 g (54% yield) of brown solid [M-13].

Example 12

Reaction of 2,7-bis(2,4,5-triphenylcyclopentadienon-3-yl)-9,9'-spyrobifluorene with 3-ethynyl-9-ethylcarbazole (Synthesis of [M-14])

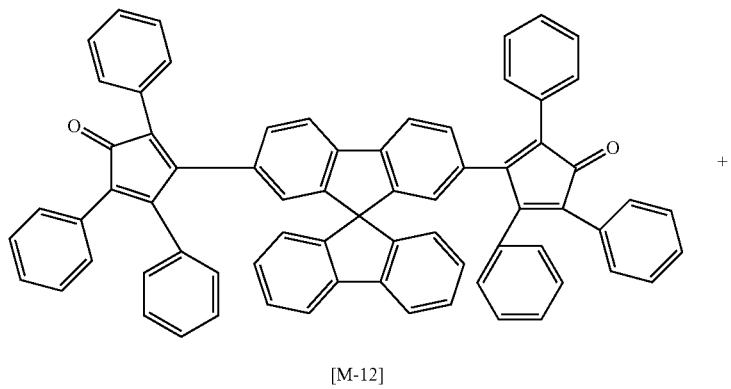

[M-12]

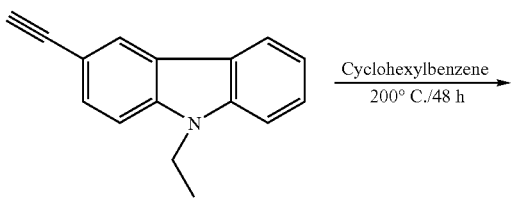

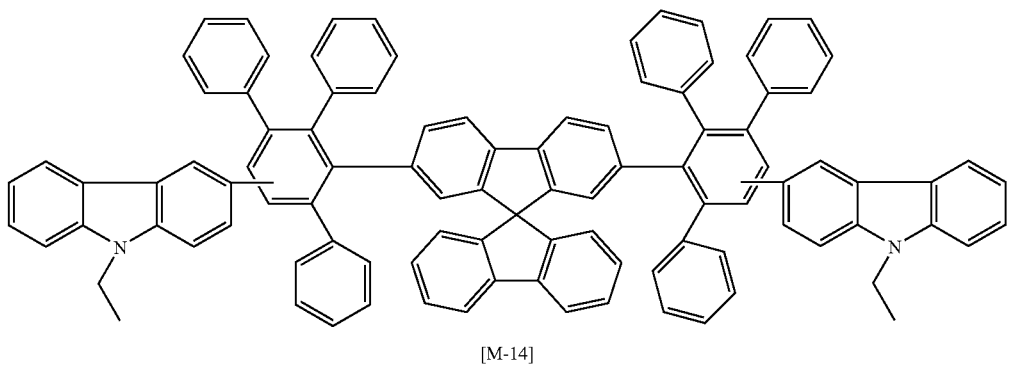

[M-14]

0.5 g (0.54 mmol) of 2,7-bis(2,4,5-triphenylcyclopentadienon-3-yl)-9,9'-spyrobifluorene and 0.24 g (1.08 mmol) of 3-ethynyl-9-ethylcarbazole were put into a 100 ml two-neck round bottom flask equipped with a stirrer, a thermometer and a reflux condenser under an argon atmosphere, and 10 ml of xylene was put thereto. The temperature of the resultant was gradually raised to 180° C., and the reaction mixture was stirred at 180° C. for 24 hours. When the reaction was completed, the reaction mixture was cooled down to room temperature and then gradually dropped into a mixture of acetone/methanol (800 ml/200 ml)), so as to precipitate a solid. The precipitated solid was filtered, dissolved in chloroform again, and re-precipitated into methanol to obtain a purified solid. This solid was filtered, thoroughly washed with a methanol and then dried sufficiently in a vacuum oven at 40° C. to give 0.44 g (63% yield) of the product [M-14] as white solid.

Example 13

Synthesis of 1,4-bis(2,4,5-triphenylthiophene)-2,5-dimethoxybenzene [M-15]

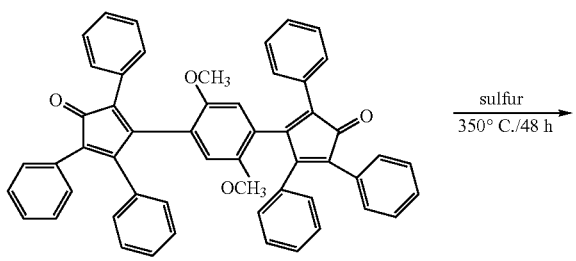

[M-15]

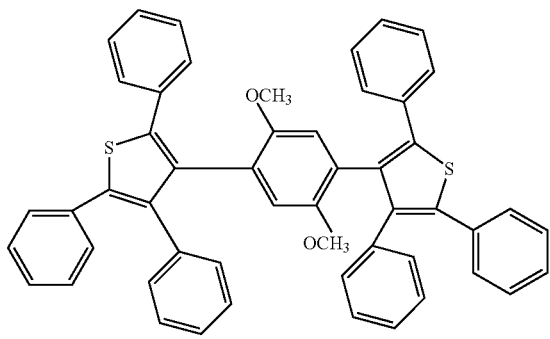

1.00 g (1.33 mmol) of 1,4-bis(2,4,5-triphenylcyclopentadienon-3-yl)-2,5-dimethoxybenzene and 0.20 g (5.88 mmol) of sulfur were put into a 50 ml ampoule flask equipped with a stirrer and a thermometer, and the flask was then sealed. The resultant was reacted at 350° C. for 48 hours. When the reaction was completed, the temperature was dropped down to room temperature, and then the ampoule was opened. The resultant was extracted with chloroform, and organic extract was washed with water several times and then dried with anhydrous magnesium sulfate. The solvent was removed to obtain a dark brown solid, which was re-crystallized from a mixture of ethyl acetate and hexane, to give brown crystal. This solid was dried sufficiently in a vacuum oven at 40° C. to give 0.58 g (57.4% yield) of [M-15].

Example 14

Synthesis of 2,7-bis(2,4,5-triphenylthiophene)-9,9'-dihexylfluorene [M-16]

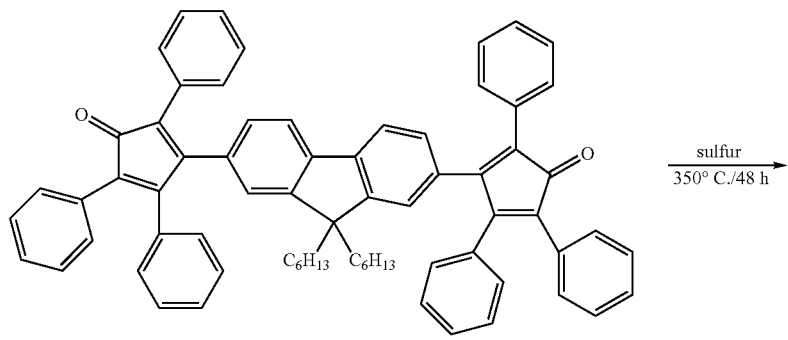

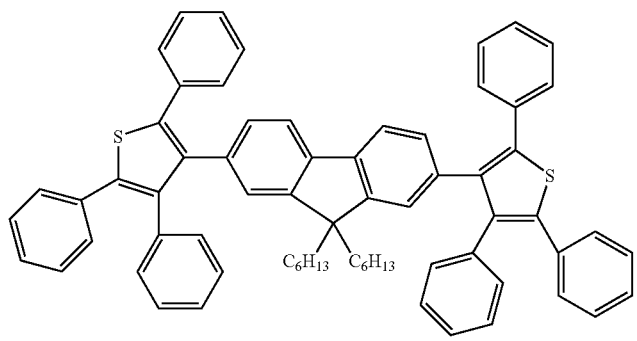

0.80 g (0.84 mmol) of 2,7-bis(2,4,5-triphenylcyclopentadienon-3-yl)-9,9'-di-n-hexylfluorene and 0.13 g (3.82 mmol) of sulfur were put into a 50 ml ampoule flask equipped with a stirrer and thermometer, and the flask was then sealed. The resultant was reacted at 350° C. for 48 hours. When the reaction was completed, the temperature was dropped down to room temperature, and the ampoule was then opened. The reaction mixture was extracted with chloroform, and then organic extract was washed with water several times and then dried with anhydrous magnesium sulfate. The solvent was removed to obtain a dark brown solid, which was re-crystallized from a mixture of ethyl acetate and hexane to give brown crystal. This solid was dried sufficiently in a vacuum oven at 40° C. to give 0.53 g (66.4% yield) of [M-16].

In chloroform, maximum UV absorption wavelength of the product was 280 nm, and maximum PL wavelength was 436 nm.

Example 15

Synthesis of 2,3,4,5-tetraphenylcyclopentadiene hydrazone [M-17]

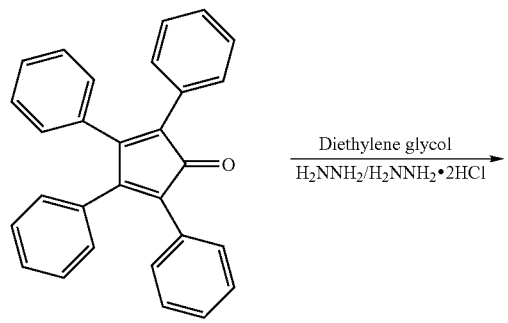

[M-17]

Diethylene glycol
H₂NNH₂/H₂NNH₂•2HCl

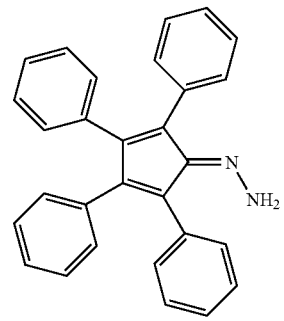

Figure 2:
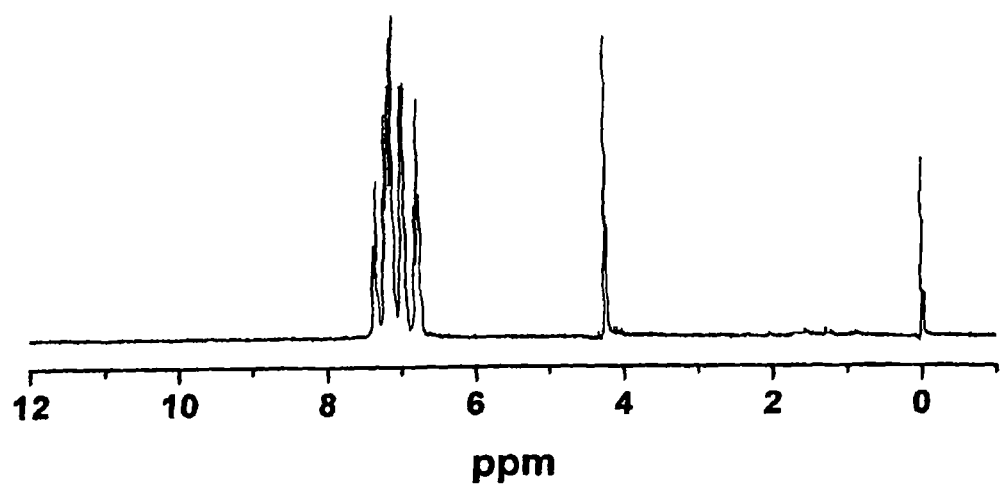
FIG. 2 is $^1$H NMR spectrum of the compound [M-17]
Figure 3:
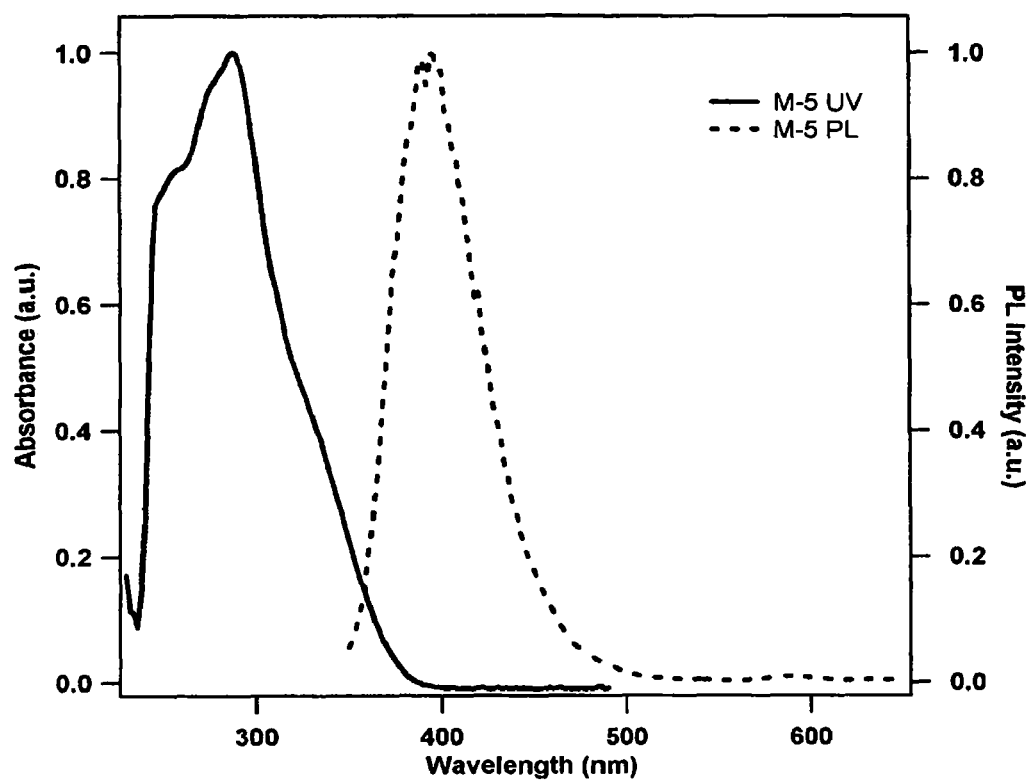
FIG. 3 is ultraviolet-visible and photoluminescence spectra of the compound [M-5]
Figure 4:
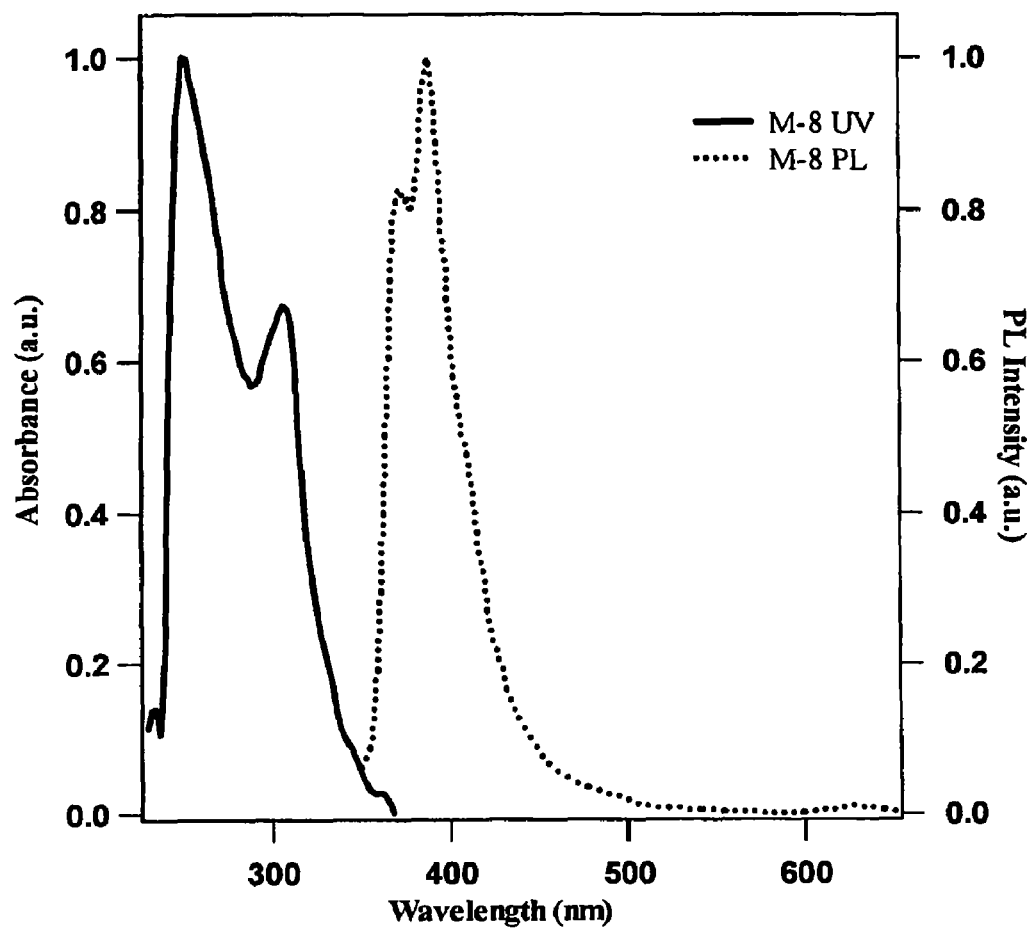
FIG. 4 is ultraviolet-visible and photoluminescence spectra of the compound [M-8]
Figure 5:
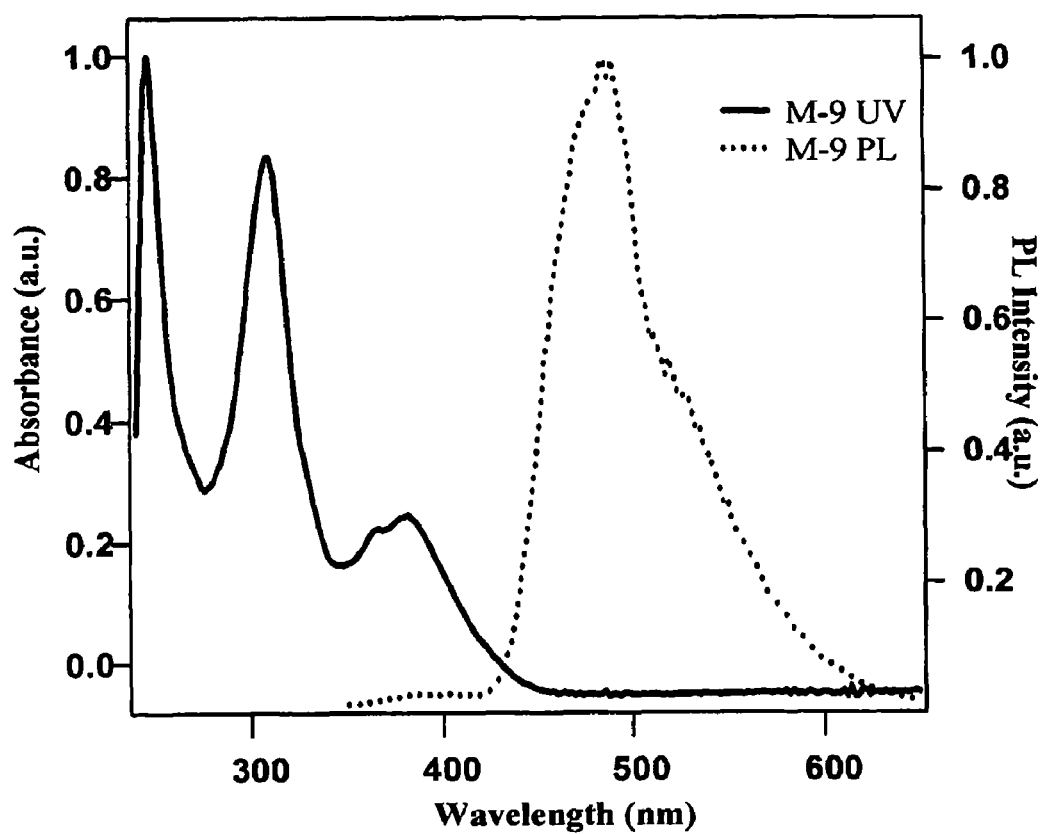
FIG. 5 is ultraviolet-visible and photoluminescence spectra of the compound [M-9]
Figure 6:
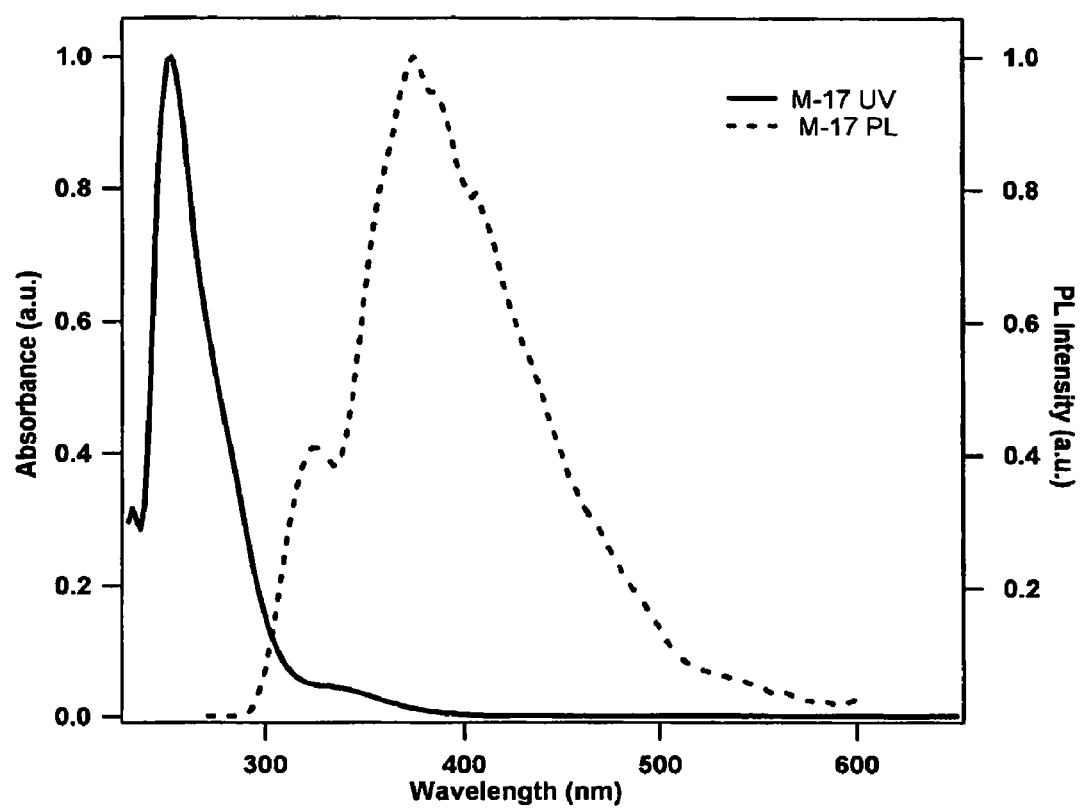
FIG. 6 is ultraviolet-visible and PL spectra of the compound [M-17]

2.0 g (5.2 mmol) of tetraphenylcyclopentadienone was put into a 500 ml two-neck round bottom flask equipped with a stirrer, a thermometer and a reflux condenser under an argon atmosphere, and 100 ml of diethylene glycol was added thereto so as to dissolve the starting material. 20 ml of hydrazine hydrate and 5.20 g of hydrazine dihydrochloride were added to the above flask, and the resultant was reacted at 200° C. for 12 hours. When the reaction was completed, the temperature was gradually dropped down to 0° C., and the reaction mixture was gradually poured into 500 ml of water to precipitate yellow solid. This solid was filtered, washed with water and then washed again with cold methanol three times. The solid was dried and then re-crystallized from ethyl acetate and hexane, to give white solid. This solid was filtered and then dried sufficiently in a vacuum oven at 40° C. to give 0.78 g (40.6% yield) of [M-17], of which melting point was 134-136° C. FIG. 2 shows $^1$H NMR spectrum of the compound [M-17].

$^1$H NMR (CDCl$_3$), δ=4.27(s, 2H, NH$_2$), 6.75-6.83 (m, 4H, aromatic), 6.98-7.01 (m, 4H, aromatic), 7.13-7.25 (m, 10H, aromatic), 7.35-7.39 (m, 2H, aromatic)

In chloroform, maximum UV absorption wavelength of the product was 252 nm, and maximum PL wavelength was 373 nm.

Example 16

Synthesis of 1,4-bis(2,3,5-triphenylcyclopentadiene hydrazone)benzene [M-18]

[M-18]

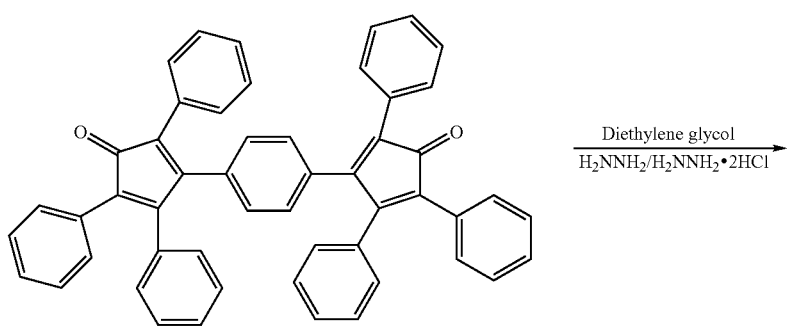

Diethylene glycol
H₂NNH₂/H₂NNH₂•2HCl

-continued

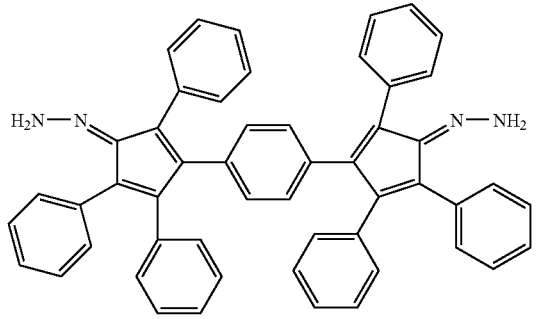

3.5 g (5.2 mmol) of 1,4-bis(triphenylcyclopentadienone) benzene was put into a 500 ml two-neck round bottom flask equipped with a stirrer, a thermometer and a reflux condenser under an argon atmosphere, and was dissolved in 100 ml of diethylene glycol. 20 ml of hydrazine hydrate and 5.20 g of hydrazine dihydro chloride were added to the above flask, and the resultant was reacted at 200° C. for 12 hours. When the reaction was completed, the temperature was gradually dropped down to 0° C., and the reaction mixture was gradually put into 500 ml of water to precipitate yellow solid. This solid was filtered, washed with water and then washed again with cold methanol three times. The solid was dried and then re-crystallized from ethyl acetate and hexane to give white solid. This solid was filtered and then dried sufficiently in a vacuum oven at 40° C. to give 0.78 g (21% yield) of [M-18].

Example 17

Test of Ultraviolet-Visible, Photoluminescence and EL Properties

The compounds prepared in Examples were respectively dissolved in chloroform, and obtained solutions were then filtered through a micro filter in size of 0.2 micron. Ultraviolet-visible (hereinafter, referred to as 'UV-Vis') and photoluminescence (hereinafter, referred to as 'PL') properties of the compound according to the present invention were determined in a manner that a UV-Vis spectrum was observed first, and then PL spectrum was observed at a wavelength in which UV-Vis peak shows maximum value.

FIGS. 3 to 6 show UV-Vis and PL spectra of the compounds [M-5], [M-8], [M-9] and [M-17], respectively.

Figure 7:
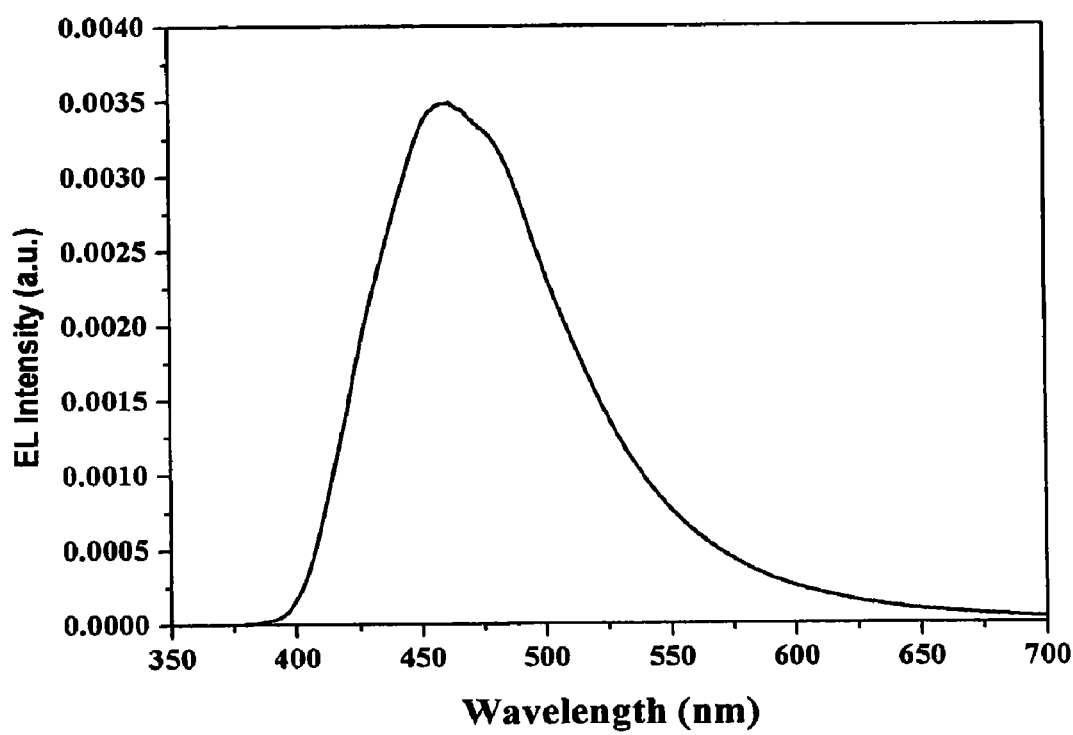
FIG. 7 is an EL spectrum of the compound [M-4].

FIG. 7 shows EL spectrum of an element comprising the compound [M-4], in construction of ITO/m-MTDATA/NPB/M-4/Alq3/LiF/Al.

As described above, according to the present invention, a compound that is derived from a compound having a cyclopentadienone group according to the present invention and that can be used as an organic light-emitting material, its preparation method and an EL element using the same are provided. The compound of the present invention can be applied as a core material of an organic EL element or the like. Besides, the compounds of the present invention can be applied for an optical switch, a sensor, a module, a waveguide, a material for an optical storage or amplification, a nonlinear optical material, a transistor, a laser, an optical conductor, a photoreceptor, an optical refracting material, a piezoelectric material, a magnetic material, a dielectric material or the like since they exhibit PL properties, nonlinear optical properties, photo and electric conductivity and the like.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A compound of formula (1):

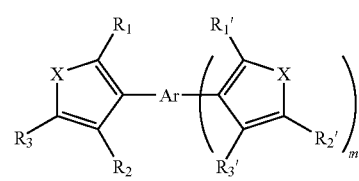

wherein m is an integer of 1-5;

X is $C=NR_1$ or $C=NNR_1R_2$;

$R_1$, $R_2$, $R_3$, $R_1'$, $R_2'$, and $R_3'$ may be the same or different from each other, and are independently selected from the group consisting of hydrogen, $C_1$-$C_{22}$ aliphatic alkyl, $C_1$-$C_{22}$ alicyclic alkyl, $C_1$-$C_{22}$, alkoxy, and $C_6$-$C_{18}$ aryl and aryloxy; and Ar is aromatic selected from the group consisting of phenylene, naphthalene, anthracene, fluorene, arylamine, and the following structures:

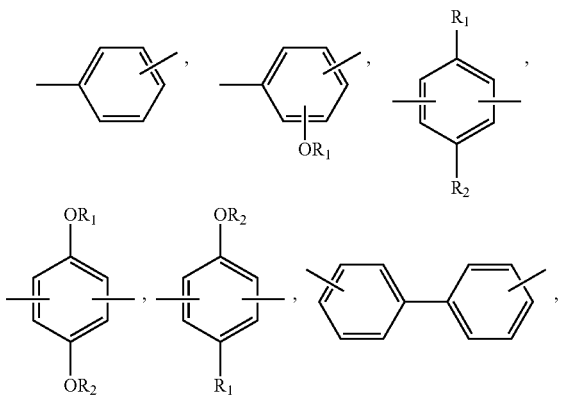

-continued

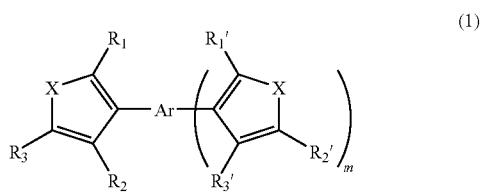

2. The compound according to claim 1, wherein $R_1$, $R_2$, $R_3$, $R_1'$, $R_2'$, and $R_3'$ are independently selected from the group consisting of hydrogen, methyl, ethyl, propyl, isopropyl, butyl, isobutyl, pentyl, hexyl, ethylhexyl, heptyl, octyl, isooctyl, nonyl, decyl, dodecyl, hexadecyl, octadecyl, dococyl, cyclopropyl, cyclopentyl, cyclohexyl, methoxy, ethoxy, butoxy, hexyloxy, methoxyethoxyethyl, methoxyethoxyethoxyethyl, cyanoethyl, carboxymethyl, phenyl, phenoxy, tolyl, benzyl, naphthyl, and anthrancenyl.

3. The compound of claim 1, wherein $R_1$, $R_2$, and $R_3$ are independently selected from hydrogen, methyl, ethyl, propyl, isopropyl, butyl, isobutyl, pentyl, hexyl, ethylhexyl, heptyl, octyl, isooctyl, nonyl, decyl, dodecyl, hexadecyl, octadecyl, dococyl, cyclopropyl, cyclopentyl, cyclohexyl, methoxy, ethoxy, butoxy, hexyloxy, methoxyethoxyethyl, methoxyethoxyethoxyethyl, cyanoethyl, carboxymethyl, phenyl, phenoxy, tolyl, benzyl, naphthyl, and anthrancenyl.

4. A compound of formula (1):

$$\text{(1)}$$

wherein m is an integer of 1-5;
X is C=$NR_1$ or C=$NNR_1R_2$;
$R_1$ and $R_1'$ are independently selected from the group consisting of hydrogen, methyl, ethyl, propyl, isopropyl, butyl, isobutyl, pentyl, hexyl, ethylhexyl, heptyl, octyl, isooctyl, nonyl, decyl, dodecyl, hexadecyl, octadecyl, dococyl, cyclopropyl, cyclopentyl, cyclohexyl, methoxy, ethoxy, butoxy, hexyloxy, methoxyethoxyethyl, methoxyethoxyethoxyethyl, cyanoethyl, carboxymethyl, phenyl, phenoxy, tolyl, benzyl, naphthyl, and anthrancenyl;
$R_2$, $R_3$, $R_2'$, and $R_3'$ may be the same or different from each other, and are independently selected from the group consisting of hydrogen, $C_1$-$C_{22}$ aliphatic alkyl, $C_1$-$C_{22}$ alicyclic alkyl, $C_{1\text{-}22}$ alkoxy, $C_6$-$C_{18}$ aryl and aryloxy; and
Ar is selected from the group consisting of phenylene, naphthalene, anthracene, and arylamine.

5. A compound of formula:

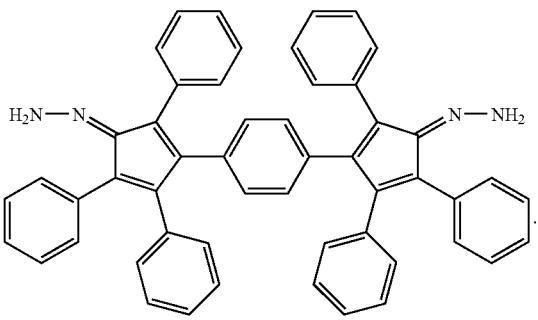

* * * * *